United States Patent [19]

Wagner et al.

[11] Patent Number: 5,362,901
[45] Date of Patent: Nov. 8, 1994

[54] PROCESS FOR THE PREPARATION OF ORGANIC CARBONATES HAVING AT LEAST ONE AROMATIC ESTER GROUP

[75] Inventors: Paul Wagner, Duesseldorf; Norbert Schön; Hans-Josef Buysch, both of Krefeld, all of Germany

[73] Assignee: Bayer Aktiengesellschaft, Leverkusen, Germany

[21] Appl. No.: 66,735

[22] Filed: May 25, 1993

[30] Foreign Application Priority Data

Jun. 1, 1992 [DE] Germany ............................ 4218061

[51] Int. Cl.⁵ ............................................. C07C 69/96
[52] U.S. Cl. ..................................... 558/270; 558/271
[58] Field of Search ................................ 558/270, 271

[56] References Cited

U.S. PATENT DOCUMENTS

| | | | |
|---|---|---|---|
| 4,410,464 | 10/1993 | Hallgren | 558/271 |
| 5,008,046 | 4/1991 | Bremus et al. | 554/170 |
| 5,210,268 | 5/1993 | Fukuoka et al. | 558/270 |

FOREIGN PATENT DOCUMENTS 0461274 12/1991 European Pat. Off. .

Primary Examiner—José G. Dees
Assistant Examiner—Dwayne C. Jones
Attorney, Agent, or Firm—Spung Horn Kramer & Woods

[57] ABSTRACT

The title compounds are prepared from organic carbonates having at least one aliphatic ester group and phenolic compounds by transesterification in the presence of a transesterification catalyst known per se at 60°–320° C. in a column-type reactor with multiple recycling of the reaction products into this reactor with intermediate storage of the product streams.

15 Claims, 1 Drawing Sheet

PROCESS FOR THE PREPARATION OF ORGANIC CARBONATES HAVING AT LEAST ONE AROMATIC ESTER GROUP

BACKGROUND OF THE INVENTION

1. Field of the Invention

The invention relates to a continuous process for the preparation of aryl carbonates from carbonates containing at least one aliphatic ester group on the one hand and phenols or alkyl aryl carbonates on the other hand by catalyzed transesterification in a column-type reactor with multiple recycling of the reaction products into the same reactor and intermediate storage of the product streams in suitable vessels.

2. Description of the Related Art

The preparation of aromatic and aliphatic-aromatic carbonates by transesterification starting from aliphatic carbonates and phenols is known in principle. This is an equilibrium reaction, the position of the equilibrium being almost completely displaced in the direction of the aliphatically substituted carbonates. Therefore, it is relatively easy to prepare aliphatic carbonates from aromatic carbonates and alcohols. However, in order to carry out the reaction in the reverse direction towards aromatic carbonates, it is necessary effectively to displace the highly unfavourable equilibrium, where not only highly active catalysts but also a favourable procedure have to be used.

A multiplicity of effective catalysts, such as alkali metal hydroxides, Lewis acid catalysts selected from the group comprising the metal halides (German Offenlegungsschrift 25 28 412 and 25 52 907), organotin compounds (EP 879, EP 880, German Offenlegungsschrift 34 45 552, EP 338 760), lead compounds (JP-57/176 932) and Lewis acid/proton acid catalysts (German Offenlegungsschrift 34 45 553) have been recommended for the transesterification of aliphatic carbonates by phenols. In the known processes the transesterification is carried out in a batch reactor under atmospheric pressure or super-atmospheric pressure, if necessary, using an additional separation column. Even using the most active catalysts, reaction times of many hours are required even to achieve mean conversions of only approximately 50% of phenol. Thus, in the batchwise transesterification of phenol with diethyl carbonate at 180° C. using various organotin compounds, as described in German Offenlegungsschrift 34 45 552, yields of diphenyl carbonate of an order of magnitude of above 20% are only achieved after a reaction time of approximately 24 hours; in the batchwise transesterification of phenol and dimethyl carbonate with the aid of organotin catalysts, as described in EP 879, the phenol conversion after 30 hours is 34% of the theoretical value.

This means that on account of the unfavourable thermodynamic conditions, the described transesterification reactions in tanks or pressure autoclaves, even with the use of highly active catalyst systems, can only be carried out highly disadvantageously in the sense of an industrial process, since very poor space-time yields and high residence times at high reaction temperatures are required, where, because of the incomplete transesterification, a high distillation effort must additionally be applied which requires further energy.

Such procedures are also particularly disadvantageous since, even using highly selective transesterification catalysts, at the high temperatures and long residence times of many hours, a significant amount of side-reactions occurs, for example ether formation and the elimination of carbon dioxide.

An attempt was therefore made to displace the reaction equilibrium as rapidly as possible in the direction of the desired products by adsorption of the alcohol forming in the transesterification to molecular sieves (German Offenlegungsschrift 33 08 921). It is shown from the description of this procedure that a large amount of molecular sieve is required for the adsorption of the reaction alcohol, which far exceeds the amount of alcohol being liberated. In addition, the molecular sieves used must be regenerated even after a short time and the conversion rate to the alkylaryl carbonate intermediates is relatively low. This method therefore also appears not to be advantageously applicable industrially.

It is known to carry out equilibrium reactions, in particular esterifications and transesterifications, in columns, to accelerate them in this manner and to displace them in the direction of the desired products (Chem.-Ing.-Techn. 49, 151 (1977); German Offenlegungsschrift 38 09 417; Chem.-Ing.-Techn. 62, 226 (1990); Ullmanns Encyclopädie der techn. Chemie [Ullmanns Enyclopaedia of Industrial Chemistry], 4th edition, volume 3, pp. 375 ff. (1973)). A continuous transesterification process described in WO 91/09832=EP 0 461 274 for the preparation of aromatic carbonates in which the reaction is carried out in a multiple step manner in sequentially connected columns is an optimized development of this reaction principle. In the columns described, phenols are reacted with dialkyl carbonates, the lower boiling reaction products, that is aliphatic alcohols, together with unreacted dialkyl carbonates being withdrawn via the head of the column and the higher boiling reaction products, that is alkyl aryl carbonates and, possibly, diaryl carbonates being withdrawn at the foot of the column. In a further downstream column, the alkyl aryl carbonates already formed are reacted to form the desired diaryl carbonate end products. The dialkyl carbonates formed as coupling products and, possibly, alcohols and the still unreacted phenols are withdrawn at the top end of the column and partly or completely recycled to the first column. However, as can be deduced from the example embodiments and the process variants described, the conversions of the phenols and dialkyl carbonates in the first transesterification column, even under favourable conditions such as high temperatures and pressures and large excesses of dialkyl carbonates of 100 to 300%, are restricted to low values, that is, even in favourable cases as in Example 10 of WO 91/09832, the bottom contains only approximately 15% by weight of transesterification products, essentially methyl phenyl carbonate.

This means that in the subsequent second column, only a small part of the starting material stream, that is the alkyl phenyl carbonate already formed, can be converted to the diaryl carbonate end product with the disadvantageous consequence that the overwhelming majority of the remainder, which is essentially composed of phenol, must be removed via the head by distillation and returned, following condensation, to the first column.

A disproportionately high distillation effort and expenditure of energy must be applied for this. The columns to be used must have large volumes for a given amount of product per unit of time and require high investment costs; in particular, distilling off the large amounts of phenol, dialkyl carbonate and, possibly, alcohol, which is preferably carried out in vacuo, large amounts of gas being formed, requires a very large column which is thus expensive and difficult to operate. Moreover, the control of a plurality of continuously operated and sequentially connected columns, whose product streams are each independent of the other, is complex and difficult.

However, the improvement, albeit unsatisfactory, achieved according to WO 91/09832 is not surprising, since it is generally known that transesterifications in columns frequently proceed more rapidly, which is just what is observed in the present case. However, the conversions obtained are very low and the assumption is apparently made that, at the unfavourable equilibrium position ($K \simeq 10^{-3}$), even under optimal conditions, that is high temperatures and pressures, they virtually cannot be further increased, that is only with very high expenditure. Such an unfavourable equilibrium position means that at equilibrium only approximately 2 to 3% by weight of the product are present and the conversion can only be further increased if a product component, here the reaction alcohol, is removed and the reaction system can reestablish equilibrium. This process would have to be repeated several times. When equilibrium is established slowly, as in the present case, very long, multiple-tray columns would have to be used which would be able to be operated only at low load and low space-time yield. Such conditions were obviously considered in WO 91/09832 as unrealizable.

The aim of an improvement of the transesterification process must therefore be to realize greater phenol conversions and lower residual contents of phenol in the bottom product than hitherto using a suitable reaction apparatus under suitable conditions in a continuous, as simple as possible procedure.

SUMMARY OF THE INVENTION

This aim can now be achieved by the semi-continuous catalyzed transesterification process according to the invention. The product stream passes repeatedly through a column-type reactor, as a result of which, surprisingly, a desired composition is obtained which contains considerably more transesterification products and less phenol. The product obtained by one passed through the column, in contrast to the abovementioned process, need not be concentrated by distillation, but is pumped back, in the liquid form obtained in the preceding pass, into the upper part of the column so that distillation effort is dispensed with. In order to be able to achieve a continuous procedure when a column is used repeatedly, the product streams are subjected to intermediate storage in a suitable vessel having two or more partitioned-off chambers and are returned to the column from each of these chambers in turn. Such a procedure requires only simple apparatus, that is in the simplest case a column, a suitable, inexpensive intermediate storage chamber and, moreover, a simple control method, which ultimately means low expense of investment. Since the starting material streams and product streams can be controlled by an interval timer, in fixed-time cycles or, for example, via preset product compositions or temperatures, the composition of a product stream representing a simple control parameter, the complexity of the control of the process is very low.

When a plurality of columns are used, as described in WO 91/09832, the associated accessory apparatuses and control units must be installed for each column, the control demanding much more complexity than in the process according to the invention, since the individual control parameters are dependent on each other in several ways. Since in the process design according to the invention, a separation by distillation of the unreacted starting materials can only take place at much higher conversions, significantly less reaction space and also less energy are required. Particularly in view of the fact that the equilibrium position for the desired aryl carbonates ($K \simeq 10^{-3}$), is extremely unfavourable, it must be surprising to the highest degree that, using the process according to the invention, such considerable increases in conversion in comparison to the prior art are possible.

The invention accordingly relates to a process for the preparation of an organic carbonate having at least one aromatic ester group of the formula

$$R^1\text{—OCOO—}R^2 \qquad (I),$$

in which
R² denotes phenyl or naphthyl or phenyl or naphthyl each of which is mono- to trisubstituted by straight-chain or branched $C_1$-$C_4$-alkyl, straight-chain or branched $C_1$-$C_4$-alkoxy, cyano and/or halogen and
R¹ can, independently of R², assume the range of meanings of R² or can denote straight-chain or branched $C_1$-$C_6$-alkyl, by catalysed reaction of 0.1–10 mol, preferably 0.2–5 mol, particularly preferably 0.5–3 mol, in each case of an organic carbonate having at least one aliphatic ester group of the formula

$$R^1\text{—OCOO—}R^3 \qquad (II),$$

in which
R³ denotes straight-chain or branched $C_1$-$C_6$-alkyl and
R¹ has the above range of meanings,
with 1 mol in each case of a phenolic compound of the formula

$$R^2\text{—OX} \qquad (III),$$

in which
R² has the above range of meanings and
X represents hydrogen or —COO—$C_1$-$C_6$-alkyl having a straight-chain or branched alkyl group,
in the presence of a transesterification catalyst known per se at 60°–320° C. in a column-type reactor, the organic carbonate containing at least one aromatic ester group being withdrawn from the bottom part of the column and the alcoholic compound co-formed as a reaction product of the formula

$$R^3\text{—OX} \qquad (IV),$$

in which
X and R³ have the meaning mentioned,
being withdrawn from the top part of the column, which is characterised in that the bottom product withdrawn in the liquid state from the bottom part of the column which contains a carbonate containing at least one aromatic ester group, still unreacted phenol and, possibly, small amounts of the carbonate containing at least one aliphatic ester group, is subjected to 1 to 10, preferably 1 to 5 further passes through the stone reactor with intermediate storage of the bottom product, where the further addition of the organic carbonate having at least one aliphatic ester group can be dispersed with in the last 1–4 passes employed.

BRIEF DESCRIPTION OF THE DRAWING

The accompanying drawing shows an arrangement of a reaction column (A) with intermediate storage facilities (B), e.g. two storage chambers (B.1) and (B.2).

DETAILED DESCRIPTION OF THE INVENTION

Figure 1:
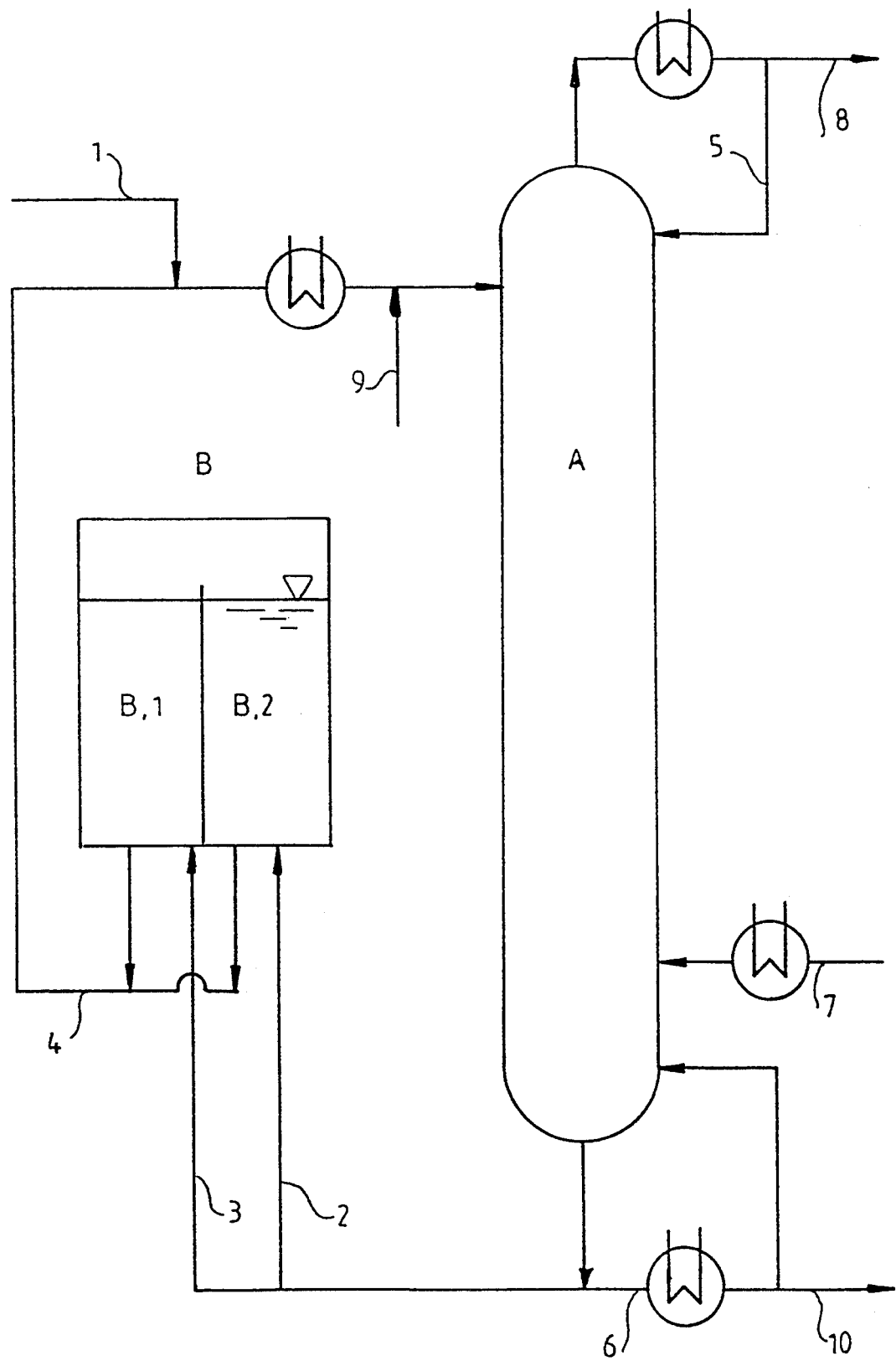

The transesterification in the process according to the invention includes a plurality of reactions, as the equations below show in a generalized form:

$$\text{Alkyl—OCOO—Alkyl} + \text{Aryl—OH} \rightarrow \text{Aryl—OCOO—Alkyl} + \text{Alkyl—OH} \quad \text{(Equation 1)}$$

$$\text{Aryl—OCOO—Alkyl} + \text{Aryl—OH} \rightarrow \text{Aryl—OCOO—Aryl} + \text{Alkyl—OH} \quad \text{(Equation 2)}$$

$$2\text{Aryl—OCOO—Alkyl} \rightarrow \text{Aryl—OCOO—Aryl} + \text{Alkyl—OCOO—Alkyl} \quad \text{(Equation 3)}$$

In the formation of a diaryl carbonate, the transesterification from the aliphatic to the aromatic ester groups proceeds in two stages, an alkyl aryl carbonate according to the meaning of Equation 1 being passed through as a product of the first transesterification stage.

Equation 3 further shows a disproportionation reaction, in which both the symmetrical dialkyl carbonate and also the desired symmetrical diaryl carbonate are formed from a mixed alkyl aryl carbonate. It is also possible to obtain the alkyl aryl carbonate as the desired reaction product, that is only to operate the first transesterification stage. It is still further possible to also obtain unsymmetrical diaryl carbonates by use of mixtures of different phenols.

Dialkyl carbonates having identical or different aliphatic ester groups having straight-chain or branched $C_1$–$C_6$-alkyl are used. Such dialkyl carbonates are known to those skilled in the art and can be prepared by known processes. To reduce costs, symmetrical dialkyl carbonates are generally used as starting materials.

Straight-chain or branched $C_1$–$C_6$-alkyl is, for example, methyl, ethyl, propyl, isopropyl, butyl, isobutyl, pentyl or hexyl.

Straight-chain or branched $C_1$–$C_4$-alkoxy is, for example, methoxy, ethoxy, propoxy, isopropoxy, butoxy or isobutoxy.

Halogen is, for example, fluorine, chlorine or bromine, preferably fluorine or chlorine, particularly preferably chlorine.

The aromatic ester group can be derived from a phenol or from a naphthol, preferably from a phenol, and can be mono- to trisubstituted in the manner described, preferably mono- or disubstituted, particularly preferably monosubstituted. The cyano substituent generally occurs only once as a substituent. The process according to the invention for the transesterification with the aid of unsubstituted phenol is of very particular importance.

Phenols which can be used according to the invention which come under formula (III) when X represents hydrogen are, for example, unsubstituted phenol, o-, m- or p-cresol, o-, m- or p-chlorophenol, o-, m- or p-ethylphenol, o-, m- or p-propylphenol, o-, m- or p-methoxyphenol, 2,6-dimethylphenol, 2,4-dimethylphenol, 3,4-dimethylphenol, 1-naphthol and 2-naphthol.

Phenols which can be preferably used are therefore generally those of the formula $$R^{12}\text{—OH} \quad \text{(V)},$$

in which $R^{12}$ denotes phenyl or phenyl monosubstituted by $C_1$–$C_4$-alkyl, $C_1$–$C_4$-alkoxy or chlorine.

Among these, unsubstituted phenol is particularly preferred.

The organic carbonates having at least one aliphatic ester group used are preferably symmetrical dialkyl carbonates of the formula $$R^3\text{—OCOO—}R^3 \quad \text{(VI)},$$

in which $R^3$ has the meaning given.

Dialkyl carbonates which can be used according to the invention are, for example, dimethyl carbonate, diethyl carbonate, dipropyl carbonate, dibutyl carbonate and dihexyl carbonate. Dialkyl carbonates which can preferably be used are dimethyl carbonate and diethyl carbonate.

Diaryl carbonates which can be prepared according to the invention are, for example, diphenyl carbonate, the symmetrically and unsymmetrically substituted isomeric biscresyl carbonates, the symmetrically and unsymmetrically substituted isomeric bis(chlorophenyl) carbonates, the symmetrically and unsymmetrically substituted isomeric bis(methoxyphenyl) carbonates, the symmetrically and unsymmetrically substituted isomeric bis(ethoxyphenyl) carbonates, bis(2,6-dimethylphenyl) carbonate, bis(2,4-dimethylphenyl) carbonate, di-1-naphthyl carbonate and di-2-naphthyl carbonate, and, moreover, further unsymmetrically substituted diaryl carbonates, for example the isomeric cresyl phenyl carbonates, the isomeric chlorophenyl phenyl carbonates, the isomeric methoxyphenyl phenyl carbonates, the isomeric naphthyl phenyl carbonates and 1-naphthyl 2-naphthyl carbonate.

Diaryl carbonates which can preferably be prepared according to the invention are those of the formulae $$R^{15}\text{—OCOO—}R^{12} \quad \text{(VII)}$$

and $$R^{12}\text{—OCOO—}R^{12} \quad \text{(VIII)},$$

in which $R^{12}$ and $R^{15}$, independently of each other, have the range of meanings given above for $R^{12}$.

A diaryl carbonate which can particularly preferably be prepared is diphenyl carbonate.

Alkyl aryl carbonates which can be prepared according to the invention are, for example, $C_1$–$C_6$-alkyl phenyl carbonates, such as methyl phenyl carbonate, ethyl phenyl carbonate, propyl phenyl carbonate, butyl phenyl carbonate and hexyl phenyl carbonate, $C_1$–$C_6$-alkyl (o-, m-, p-cresyl) carbonates, such as methyl o-cresyl carbonate, methyl p-cresyl carbonate, ethyl o-cresyl carbonate, ethyl p-cresyl carbonate, $C_1$–$C_6$-alkyl (o-, m-, p-chlorophenyl) carbonates, such as methyl p-chlorophenyl carbonate or ethyl p-chlorophenyl carbonate and analogous compounds. Alkyl aryl carbonates which can particularly preferably be prepared are methyl phenyl carbonate and ethyl phenyl carbonate.

According to the invention, the bottom product after the first pass through the column is subjected to at least one further pass, generally 1 to 10 further passes, preferably 1 to 5 further passes. The bottom product withdrawn remains in the liquid phase; a concentration by distillation is thus dispensed with. The bottom product remains approximately at the temperature it was withdrawn at so that the perceptible heat remains in the system.

In a form particularly expedient with respect to the use of apparatus, the bottom product is returned to one or up to 10 further passes in the same column, for which purpose an intermediate storage is undertaken (continuous semi-batch process). This multiple-phase procedure is described with reference to FIG. 1.

In a first phase, a phenol is fed in via the line (1), if desired, together with a catalyst, at the head of column (A) and a dialkyl carbonate is conducted via (7) in the gaseous phase in the opposite direction to this from the foot of the column. The dialkyl carbonate stream conducted in counter-current can contain, to a minor extent, the underlying alcohol, preferably <5% by weight and particularly preferably <1% by weight, based on the total dialkyl carbonate stream. However, an alcohol-free metering in of dialkyl carbonate at (7) is very particularly preferred. The low-boiling products are withdrawn at the head of the column via the line (8) and the high-boiling reaction products are withdrawn at the foot of the column and passed via (2) or (3) into a chamber (B.1) of the intermediate store (B), until this is full. The intermediate store can also be composed of a plurality of tanks, of which only 2, that is (B.1) and (B.2), are depicted in FIG. 1.

The phenol feed (1) is then interrupted in the second phase and the product subjected to intermediate storage is returned via (4) to the top end of the column, during which, dialkyl carbonate can again be metered in counter-current via (7). The product leaving at the column foot during this time is now collected in a second intermediate storage tank (B.2), until this is full. The mixtures of intermediates contained in the storage tanks (B.1) or (B.2) can now be alternately circulated with a counter-current of dialkyl carbonate until a desired degree of transesterification or phenol consumption, which can be >5% by weight, preferably >20% by weight, and particularly preferably >30% by weight of phenol, based on the total transesterification mixture, is achieved. In a third phase, the mixture of intermediates is then circulated via (4) in the same manner as above, but without a counter-current of dialkyl carbonate, until the alkyl aryl carbonate present is almost completely converted to the desired diaryl carbonate. In a fourth and then last phase, it is, if desired, possible to eliminate any phenol or alkyl aryl carbonate present by distillation via the head and that is likewise via (8), the product mixture being further circulated in the described manner through the column and either the temperature being raised or the pressure in the column being reduced. At the end of these steps, the now already almost pure product, which can, possibly, still contain the catalyst, is delivered at the foot of the column via (10) and if desired is fed to a purification stage. The size of the intermediate storage vessel to be used depends on the desired amount of product and the time required for the reaction.

(5) denotes reflux to the column; (6) is the circuit through the bottom reboiler. At (9), catalyst can be added as required. The heat exchangers have not been numbered; they are familiar to those skilled in the art as are pumps and valves which are not shown.

Furthermore, with the procedure according to the invention, it is obviously also possible only to carry out a part of the described reaction phases, for example an alkyl aryl carbonate being reacted either with a phenol in the sense of a transesterification according to equation 2 or with itself in the sense of a disproportionation reaction according to equation 3 to form diaryl carbonates, no dialkyl carbonate being supplied in counter-current, as described in phase 4. It is likewise possible to realise only phases 1 and 2, that is the reaction of phenols with dialkyl carbonates.

The column-type reactor to be used is, in the simplest case, an isothermically heated tube, filled with conventional dumped or arranged packings to be used for distillations, to the head of which is fed the phenol which, if desired, can contain the catalyst in dissolved form. The dialkyl carbonate to be used is supplied in counter-current from below in vapour form. The low-boiling products, the reaction alcohols and dialkyl carbonates, are continuously withdrawn at the head of the column, the high-boiling products, alkyl phenyl carbonate, phenols and, possibly, diaryl carbonates are continuously withdrawn at the lower end of the column and are passed to an intermediate store having two or more divided-off chambers.

The column can contain, at the lower end, a stripping part operating at relatively high temperatures in which a substantial to complete separation is performed of the added dialkyl carbonate from the liquid phase trickling down, the dialkyl carbonate being returned in the vapour phase into the transesterification region of the column. In addition, the column can comprise an enrichment part at the upper part, which separates off co-evaporated phenol or alkyl phenyl carbonate from the low-boiling reaction alcohols or dialkyl carbonates and returns them in-liquid form to the transesterification part of the column.

When relatively large columns are used, it is expedient to introduce the energy necessary for the reaction not via jacket heating, but with both the phenol used and with the dialkyl carbonate fed in the gaseous state. The heating energy for the phenol to be added and the evaporation energy for the dialkyl carbonate can be supplied via separate evaporators or evaporators integrated into the column. In the central part of the column, in which the majority of the transesterification proceeds, an enlargement of the column diameter up to four times that of the remaining parts can be advantageous. In addition, internal or external heat exchangers can be installed in the column to compensate for the heats of reaction. The column can have either the same temperature or a temperature gradient over the entire length. The design of the transesterification, stripping and enrichment part can be undertaken by those skilled in the art.

The dumped or arranged packings to be used are those conventional per se for distillations, such as are described, for example, in Ullmann's Encylopädie der Technischen Chemie [Ullmann's Encyclopaedia of Industrial Chemistry], 4th edition, volume 2, pp. 528 ff. or in the manufacturers' pamphlets from the relevant apparatus manufacturers. Examples which may be mentioned are: Raschig and Pall rings, Berl, Intalox or torus saddles, Interpack packings made of various materials, such as glass, stoneware, porcelain, stainless steel or plastic, which, in particular when metal is used, can be made up by weaving or knitting. Dumped and arranged packings are preferred which have a large surface area, good wetting and sufficient residence time of the liquid phase.

These are, for example, Pall and Novalox rings, Berl saddles, BX packings, Montz pack, Mella pack, Melladur, Kera pack and CY packings.

However, suitable for the process according to the invention are not only packed columns but preferably those having fixed internals. Those suitable are generally tray columns, for example those having sieve trays, bubble-cap trays, valve trays, tunnel trays and centrifugal trays which can, furthermore, occur in different designs. Among these, those equipped with bubble-cap trays or valve trays having high residence times with good mass transfer, for example those having high overflow weirs, are particularly preferred.

The column is operated such that the phenol or an alkyl aryl carbonate which, if desired, contains the catalyst in dissolved and suspended form, is fed in as a liquid into the upper half, preferably the upper third, preferably at the temperature prevailing at this position in the column. Alternatively, the catalyst can also be introduced separately in dissolved form in the reaction alcohol or in a suitable inert solvent external to the system. When heterogeneous catalysts are used, these can be used in a mixture with the dumped packings mentioned, in a suitable form in place of dumped packings or as a bed on installed column trays. The dialkyl carbonate, generally in vapour form, is fed into the lower half of the column, preferably above a stripping zone possibly present. It can, furthermore, be expedient to additionally feed mixtures of dialkyl carbonates and the reaction alcohols, whose composition corresponds to that of the vapour phase at this position in the column, at a position above the dialkyl carbonate metering in.

A further expedient procedure comprises withdrawing the gas phase at one or more positions of the column and replacing it by fresh gaseous dialkyl carbonate. After passing through the transesterification zone, the reaction alcohol, preferably after passing through an enrichment zone, is withdrawn at the head of the column. It generally still contains excess or unreacted dialkyl carbonate. After a single pass through the transesterification zone and, preferably, a stripping part, a mixture of alkyl aryl carbonate with excess or unreacted phenol, possibly small amounts of already formed dialkyl carbonate and, possibly, soluble catalysts leave at the foot of the column.

This mixture is collected in a chamber of a vessel containing a plurality of divided-off chambers until the chamber is full, the mixture being preferably kept at about the temperature prevailing inside the column in the liquid phase, which can be effected by insulation or separate heating. It is then fed back to the column via line (4), the feeding of fresh phenol or alkyl aryl carbonate via (1) being interrupted. The product mixture produced at the column foot during this time is collected in a second separate chamber of the vessel. In this manner, the above-described reaction phases can be carried out one after the other. It is possible, and in many cases expedient, to increase the temperature and, if desired, the pressure as the reaction proceeds, particularly during the third phase of the process.

The molar ratio of the starting materials used in the column varies from 0.1–10 mol, preferably from 0.2–5 mol and particularly preferably from 0.5–3 mol of dialkyl carbonate per mole of phenol used.

The process according to the invention can be carried out at temperatures of 60°–320° C., preferably at temperatures of 120°–250° C. and, particularly preferably, at temperatures of 140°–240° C. in the column. A temperature gradient to be preferably applied lies in the temperature range given and increases from the column head in the direction of the column foot. In this case, it must be ensured that the reaction temperature in the transesterification region is not above the evaporation temperature of the phenol used. It is therefore advantageous to carry out the transesterification according to the invention not only at atmospheric pressure but also at elevated or reduced pressure from 50 mbar to 20 bar. A preferred pressure range is between 0.8 and 15 bar, a particularly preferred pressure range is between 1 and 10 bar.

The space-time loading of the column is 0.05–10 g of the entire amount of reactants per ml of effective column volume per hour, preferably 0.1–5 g/ml/h, particularly preferably 0.2–3 g/ml/h; the effective column volume in this case is that of the dumped packing or the volume in which fixed internals are located.

Catalysts which are useful for the process according to the invention and which can be identical for all phases of the process according to the invention are known in the literature. Such catalysts are, for example, hydrides, oxides, hydroxides, alcoholates, amides or salts of alkali (alkaline earth) metals, such as lithium, sodium, potassium, rubidium, caesium, magnesium and calcium, preferably of lithium, sodium, potassium, magnesium and calcium, particularly preferably of lithium, sodium and potassium (U.S. Pat. No. 3,642,858, U.S. Pat. No. 3,803,201, EP 1082). When the alcoholates are used, these can also be formed in situ according to the invention by use of the elemental alkali metals and the alcohol to be reacted according to the invention. Salts of the alkali (alkaline earth) metals can be those of organic or inorganic acids, such as acetic acid, propionic acid, butyric acid, benzoic acid, stearic acid, carbonic acid (carbonates or hydrogen carbonates), hydrochloric acid, hydrobromic acid or hydriodic acid, nitric acid, sulphuric acid, hydrofluoric acid, phosphoric acid, hydrocyanic acid, thiocyanic acid, boric acid, stannic acid, $C_1$–$C_4$-stannonic acids or antimonic acids. Compounds of the alkali (alkaline earth) metals which are preferably suitable are the oxides, hydroxides, alcoholates, acetates, propionates, benzoates, carbonates and hydrogen carbonates; hydroxides, alcoholates, acetates, benzoates or carbonates are particularly preferably used.

Such alkali (alkaline earth) metal compounds (possibly formed in situ from the free alkali metals) are used in amounts of 0.001 to 2% by weight, preferably 0.005 to 0.9% by weight, particularly preferably 0.01 to 0.5% by weight, based on the reaction mixture to be reacted.

Other catalysts which may be used according to the invention are Lewis acid metal compounds such as $AlX_3$, $TiX_3$, $UX_4$, $TiX_4$, $VOX_4$, $VX_5$, $ZnX_2$, $FeX_3$ and $SnX_4$, in which X represents halogen, acetoxy, alkoxy or aryloxy (German Offenlegungsschrift 2 528 412, 2 552 907), for example titanium tetrachloride, titanium tetraphenoxide, titanium tetraethoxide, titanium tetraisopropylate, titanium tetradodecylate, tin tetraisooctylate and aluminium triisopropylate, in addition organotin compounds of the general formula $(R^4)_{4-x}$—Sn—$(Y)_x$, in which Y represents a radical $OCOR^5$, OH or OR, where $R^5$ denotes $C_1$–$C_{12}$-alkyl, $C_6$–$C_{12}$-aryl or $C_7$–$C_{13}$-alkylaryl and $R^4$, independently of $R^5$, can have the range of meanings of $R^5$ and x denotes an integer from 1 to 3, dialkyltin compounds having 1–12 C atoms in the alkyl radical or bis(trialkyltin) compounds, for example trimethyltin acetate, triethyltin benzoate, tributyltin acetate, triphenyltin acetate, dibutyltin diacetate, dibutyltin dilaurate, dioctyltin dilaurate, dibutyltin adipate, dibutyldimethoxytin, dimethyltin glycolate, dibutyldiethoxytin, triethyltin hydroxide, hexaethyldistannoxane, hexabutyldistannoxane, dibutyltin oxide, dioctyltin oxide, butyltin triisooctylate, octyltin triisooctylate, butylstannonic acid and octylstannonic acid in amounts of 0.001 to 20% by weight (EP 0 000 879, 0 000 880, 0 039 452, German Offenlegungsschrift 3 445 555, JP 79/63 023), polymeric tin compounds of the formula —[—R$^4$, R$^5$Sn—O—]—, for example poly[oxy(dibutylstannylene)], poly[oxy(dioctylstannylene)], poly[oxy(butylphenylstannylene)] and poly[oxy(diphenylstannylene)] (German Offenlegungsschrift 3 445 552), polymeric hydroxystannoxanes of the formula —[—R$^4$Sn(OH)—O—]—, for example poly(ethylhydroxystannoxane), poly(butylhydroxystannoxane), poly(octylhydroxystannoxane), poly(undecylhydroxystannoxane) and poly(dodecylhydroxystannoxane) in amounts of 0.001 to 20% by weight, preferably from 0.005 to 5% by weight, based on carbonic diester (DE 40 06 520). Other tin compounds which can be used according to the invention are Sn(II)oxide or have the formula $$X^1\text{—Sn}(R^4)_2\text{—O—Sn}(R^4)_2\text{—}X^2 \qquad (IX),$$

in which

X$^1$ and X$^2$ independently of each other, denote OH, SCN, OR$^4$, OCOR$^4$ or halogen and R$^4$ denotes alkyl or aryl (EP 0 338 760).

Other catalysts which may be used according to the invention are lead compounds, possibly together with triorganophosphines, a chelate compound or an alkali metal halide, for example Pb(OH)$_2$.2PbCO$_3$, Pb(O-CO—CH$_3$)$_2$, Pb(OCO—CH$_3$)$_2$.2LiCl, Pb(O-CO—CH$_3$)$_2$.2PPh$_3$ in amounts from 0.001 to 1, preferably from 0.005 to 0.25 mol per mole of carbonate (JP 57/176 932, JP 01/093 580), other lead(II) and lead(IV) compounds such as PbO, PbO$_2$, red lead oxide, plumbites (PbO$^{2-}$) and plumbates (PbO$^-$) (JP 01/093 560), iron(III) acetate (JP 61/172 852), in addition copper salts and/or metal complexes, for example of alkali metals, zinc, titanium and iron (JP 89/005 588), combinations of Lewis acids and proton acids (German Offenlegungsschrift 3 445 553) or compounds of the elements Sc, Cr, Mo, W, Mn, Au, Ga, In, Bi, Te and lanthanides (EP 0 338 760).

Furthermore, heterogeneous catalyst systems can also be used in the processes according to the invention. Such systems are, for example, mixed oxides of silicon and titanium which can be prepared by joint hydrolysis of silicon halides and titanium halides (JP 54/125 617) and titanium dioxides having a high BET surface area >20 m$^2$/g (German Offenlegungsschrift 40 36 594).

Catalysts which can preferably be used in the process according to the invention are tin compounds, titanium compounds and zirconium compounds and the abovementioned alkali metal compounds and alkaline earth metal compounds; catalysts which can be particularly preferably used are organotin compounds and titanium tetraalcoholates and tetraphenolates.

The amounts of catalyst to be used are 0.01 to 10 mol %, preferably 0.05 to 5 mol % and particularly preferably 0.01 to 2 mol %, based on the phenol component or alkyl aryl carbonate component used and some can differ from the amounts mentioned in the literature.

The following examples are intended to describe the present invention in concrete terms, but it is not intended to be restricted to these examples.

EXAMPLE 1

A liquid mixture of 150 g/h of phenol and 0.5 mol % of poly[oxy(butylhydroxystannylene)](-[-BuSn(OH-)—O-]$_n$), preheated to 160° C., was continuously metered at the head into a column 185 cm in length and 28 mm in diameter isothermically thermostatted to 180° C. and filled with V4A stainless steel wire mesh rings (3×3 mm). 150 g/h of gaseous dimethyl carbonate were supplied in counter-current to this liquid stream, which dimethyl carbonate had been vaporised in a separate apparatus and fed into the column 35 cm above the column foot. At the top end of the column, which had a short enrichment part (15 cm adiabatic column equipped with a reflux divider), a mixture of methanol and dimethyl carbonate (head product) was continuously withdrawn, at the foot of the column, which had a short stripping part (35 cm oil-heated tube coil evaporator), 162 g/h of a mixture of 15.1% by weight of methyl phenyl carbonate, 1.6% by weight of diphenyl carbonate, 83.3% by weight of phenol and the catalyst (bottom product) were continuously withdrawn. The bottom product collected in a period of 4.5 h was subjected to intermediate storage and after completion of the first pass, was again fed to the head of the column at the same space-time loading and gaseous dimethyl carbonate was supplied in counter-current to this under conditions unchanged from the first pass. 173 g/h of a mixture of 26.3% by weight of methyl phenyl carbonate, 7.9% by weight of diphenyl carbonate and 65.8% by weight of phenol were now withdrawn at the column foot together with the catalyst (second pass). In a third pass of the product obtained from the second pass with a counter-current of dimethyl carbonate, 180 g/h of a bottom product of composition 28.6% by weight of methyl phenyl carbonate, 10.5% by weight of diphenyl carbonate and 60.8% by weight of phenol were obtained. This corresponds to a space-time yield for the methyl phenyl carbonate and diphenyl carbonate formation, based on three column passes, of 0.021 kg l$^{-1}$ h$^{-1}$. When this mixture was then fed a fourth time in at the head of the column, without a counter-current of dimethyl carbonate, 196 g/h of a bottom product of composition 8.8% by weight of methyl phenyl carbonate, 34.7% by weight of diphenyl carbonate and 56.4% by weight of phenol were obtained, which gives a space-time yield for the formation of methyl phenyl carbonate and diphenyl carbonate, based on 4 column passes, of 0.020 kg l$^{-1}$ h$^{-1}$.

EXAMPLE 2

The same procedure was selected as in Example 1. However, the reactor used was a 20-tray bubble-cap tray column 2 m in length and 5 cm in diameter. 500 g/h of phenol and 0.5 mol % of poly[oxy(butylhydroxystannylene)] were added at the head of the column, 500 g/h of gaseous dimethyl carbonate were added at the foot of the column. After one pass through the column, 554 g/h of a bottom product of composition 23.2% by weight of methyl phenyl carbonate, 2.1% by weight of diphenyl carbonate and 74.7% by weight of phenol were obtained, which still contained the catalyst. After a second pass of this product in the manner described in Example 1, 615 g/h of a bottom product of composition 36.8% by weight of methyl phenyl carbonate, 9.1% by weight of diphenyl carbonate and 54.1% by weight of phenol were obtained. After a third column pass, 670 g/h of a bottom product of composition 45.5% by weight of methyl phenyl carbonate, 14.3% by weight of diphenyl carbonate and 40.2% by weight of phenol were obtained. This corresponds to a space-time yield for the formation of methyl phenyl carbonate and diphenyl carbonate, based on three column passes, of 0.034 kg $l^{-1}h^{-1}$. After the fourth pass of the bottom product, in which no dimethyl carbonate was conducted in counter-current, the bottom product had the composition 13.5% by weight of methyl phenyl carbonate, 50.7% by weight of diphenyl carbonate and 35.8% by weight of phenol, which gives a space-time yield for the formation of methyl phenyl carbonate and diphenyl carbonate, based on 4 column passes, of 0.032 g $l^{-1}h^{-1}$. Here also, the catalyst was not removed at any stage, but recycled in all passes with the bottom product. The bottom compositions were determined by gas chromatographic analysis (GC) as % by weight compositions.

It is seen from the experiments described that, using the process according to the invention, high phenol conversions can be realized or products having low contents of phenol and high contents of transesterification products are achieved. Thus the proportion of transesterification products in the final product of Example 2 is approximately 65% by weight. This is considerably more than demonstrated in WO 91/09832, where only approximately 16% by weight of transesterification products are obtained. These very good conversions are obtained at the same or better overall space-time yields: in the above experiments, space-time yields of 0.02 kg $l^{-1}h^{-1}$, or 0.032 kg $l^{-1}h^{-1}$, based on the sum of methyl phenyl carbonate and diphenyl carbonate over 4 column passes, were achieved in comparison to space-time yields of 0.018 or 0.015 kg $l^{-1}h^{-1}$, as described in WO 91/09832. This means that according to the invention, using only one column which has a reaction volume comparable to that of the apparatus in WO 91/09832, at least the same amounts of aryl carbonates can be prepared per unit of time.

What is claimed is:

1. A process for the preparation of an organic carbonate having at least one aromatic ester group of the formula $$R^1-OCOO-R^2,$$

in which
$R^2$ denotes an unsubstituted phenyl or an unsubstituted naphthyl or phenyl or naphthyl each of which is mono- to trisubstituted by straight-chain or branched $C_1$-$C_4$-alkyl, straight-chain or branched $C_1$-$C_4$-alkoxy, cyano and/or halogen and
$R^1$ can, independently of $R^2$, assume the range of meanings of $R^2$ or can denote straight-chain or branched $C_1$-$C_6$-alkyl,
by catalysed reaction of 0.1–10 mol in each case of an organic carbonate having at least one aliphatic ester group of the formula $$R^1-OCOO-R^3,$$

in which $R^3$ denotes straight-chain or branched $C_1$-$C_6$-alkyl and
$R^1$ has the above range of meanings,
with 1 mol in each case of a phenolic compound of the formula $$R^2-OX,$$

in which
$R^2$ has the above range of meanings and
X represents hydrogen or $-COO-C_1$-$C_6$-alkyl having a straight-chain or branched alkyl group,
in the presence of a transesterification catalyst at 60°–320° C. in a column-type reactor, the organic carbonate containing at least one aromatic ester group being withdrawn from the bottom part of the column and the alcoholic compound co-formed as a reaction product of the formula $$R^3-OX,$$

in which
X and $R^3$ have the meaning mentioned,
being withdrawn from the top part of the column wherein the bottom product withdrawn in the liquid state from the bottom part of the column which contains a carbonate containing at least one aromatic ester group, still unreacted phenol and, possibly, small amounts of the carbonate containing at least one aliphatic ester group, is subjected to 1 to 10 further passes through the same reactor with intermediate storage of the bottom product, where the further addition of the organic carbonate having at least one aliphatic ester group can be dispensed with in the last 1–4 passes employed.

2. The process of claim 1, wherein 0.2–5 mol of the organic carbonate having at least one aliphatic ester group is reacted with 1 mol of the phenolic compound.

3. The process of claim 2, wherein 0.5–3 mol of the organic carbonate having at least one aliphatic ester group is reacted with 1 mol of the phenolic compound.

4. The process of claim 1 wherein the bottom product is subjected to 1 to 5 further passes through the same reactor.

5. The process of claim 1, wherein a phenolic compound of the formula $$R^{12}-OH$$

is used, in which
$R^{12}$ denotes phenyl or phenyl monosubstituted by $C_1$-$C_4$-alkyl, $C_1$-$C_4$-alkoxy or chlorine.

6. The process of claim 1, wherein dimethyl carbonate and phenol are reacted to form methyl phenyl carbonate and diphenyl carbonate.

7. The process of claim 1, wherein a symmetrical dialkyl carbonate of the formula $$R^3-OCOO-R^3$$

is used, in which
$R^3$ denotes straight-chain or branched $C_1$-$C_6$-alkyl.

8. The process of claim 1, wherein the reaction is carried out at 120°–250° C.

9. The process of claim 8, wherein the reaction is carried out at 140°–240° C.

10. The process of claim 1 wherein the reaction is carried out at a pressure of from 50 mbar to 20 bar.

11. The process of claim 10, wherein the reaction is claimed out at a pressure of from 0.8 to 15 bar.

12. The process of claim 11, wherein the reaction is carried out at a pressure of from 1 to 10 bar.

13. The process of claim 1, wherein the reaction is carried out at a space-time loading of the column of 0.05–10 g/ml/hr.

14. The process of claim 13, wherein the column loading is 0.1–5 g/ml/h.

15. The process of claim 14, wherein the column loading is 0.2–3 g/ml/h.

* * * * *